United States Patent
Ross et al.

(10) Patent No.: US 6,752,827 B2
(45) Date of Patent: Jun. 22, 2004

(54) DEVICES, SYSTEMS, AND METHODS FOR SUBCUTANEOUSLY PLACING AN ARTICLE

(75) Inventors: John R. Ross, Bamberg, SC (US); James R. Tobul, Bamberg, SC (US)

(73) Assignee: Vasca, Inc., Tewksbury, MA (US)

( * ) Notice: Subject to any disclaimer, the term of this patent is extended or adjusted under 35 U.S.C. 154(b) by 284 days.

(21) Appl. No.: 10/006,925

(22) Filed: Dec. 4, 2001

(65) Prior Publication Data

US 2003/0125789 A1 Jul. 3, 2003

(51) Int. Cl.⁷ .................................................. A61F 2/06
(52) U.S. Cl. ...................... 623/1.23; 606/108; 623/1.11
(58) Field of Search ................................. 606/108, 200, 606/191, 198; 623/1.11, 1.23

(56) References Cited

U.S. PATENT DOCUMENTS

| | | |
|---|---|---|
| 4,409,172 A | 10/1983 | Ward, Jr. et al. |
| 4,453,928 A | 6/1984 | Steiger |
| 4,604,762 A | 8/1986 | Robinson |
| 4,675,361 A | 6/1987 | Ward, Jr. |
| 4,731,073 A | 3/1988 | Robinson |
| 4,861,830 A | 8/1989 | Ward, Jr. |
| 5,300,106 A | 4/1994 | Dahl et al. |
| 5,840,240 A | 11/1998 | Stenoien et al. |
| 5,866,217 A | 2/1999 | Stenoien et al. |
| 6,093,194 A * | 7/2000 | Mikus et al. ............... 606/108 |

* cited by examiner

*Primary Examiner*—Tan-Uyen T. Ho
(74) *Attorney, Agent, or Firm*—Townsend and Townsend and Crew LLP

(57) ABSTRACT

A system and method for positioning an article, such as a graft or catheter, in a subcutaneous tunnel between skin and muscle tissue of a patient. The system comprises a tunneling tool, a pair of nested tubes coupleable to a trailing end of the tunnel tool, and a flexible article which can be slidably received within the pair of nested tubes. The nested tubes each have a leading end, a trailing end, and a longitudinal opening.

9 Claims, 10 Drawing Sheets

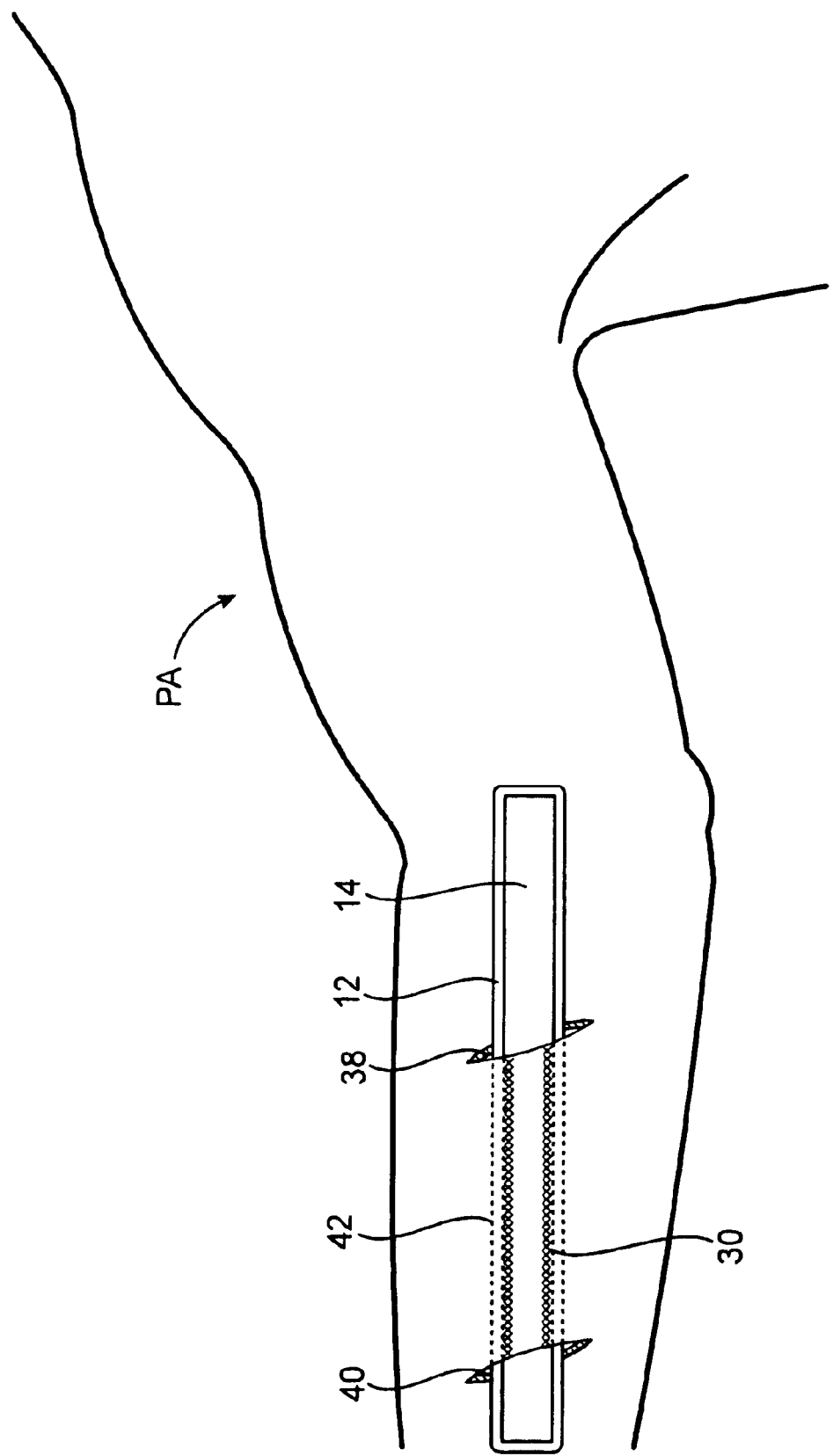

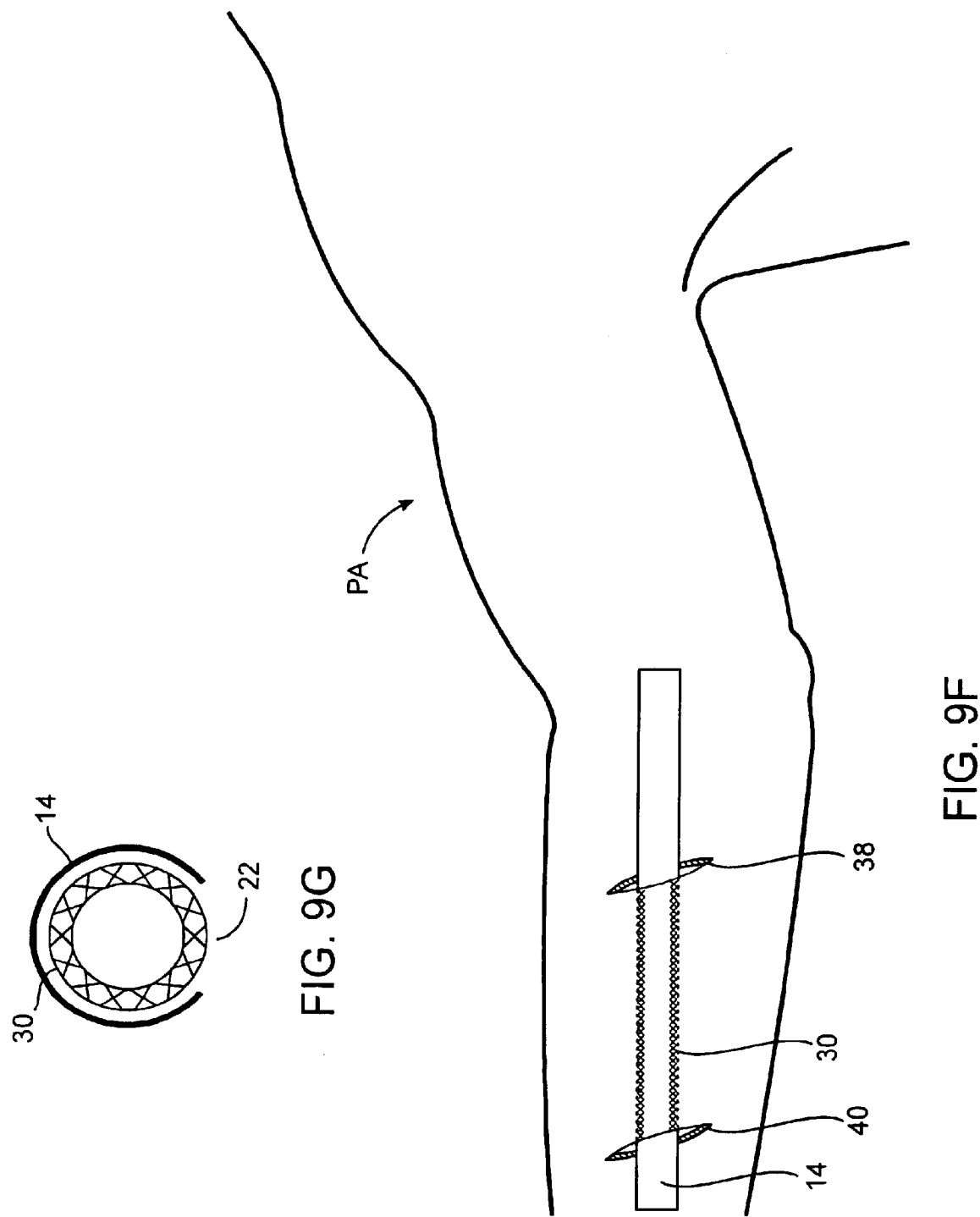

ND METHODS FOR
DEVICES, SYSTEMS, AND METHODS FOR SUBCUTANEOUSLY PLACING AN ARTICLE

BACKGROUND OF THE INVENTION

1. Field of Invention

The present invention relates generally to medical devices, systems, and methods. More particularly, the present invention provides devices, systems, and methods for positioning an article, such as a graft or catheter, in a subcutaneous tunnel between skin and muscle tissue of a patient to establish improved access to the patient's vascular system for hemodialysis, hemofiltration, or other extracorporeal blood treatments.

Significant attention has been focused on the specific needs of vascular access for hemodialysis. Hemodialysis is generally the only treatment alternative for patients unable to receive a kidney transplant due to medical conditions, age, or absence of a donor. Hemodialysis, in part, takes up the excretory role of the kidney by drawing blood from the arterial system into a membrane separation device outside of the body, which transfers noxious substances from the blood into dialysate for disposal and returns the cleansed blood into the venous system of the patient. Hemodialysis and other extracorporeal treatment regimens that are repeated periodically, often for the lifetime of the patient, regularly utilize vascular grafts or catheters to improve blood flow characteristics. Vascular grafts, such as the Perma-Seal™ graft available from Possis Medical, Inc. and the VAG™ (venous arterial graft) available from Thoratec Laboratories Corporation, are permanently implanted in a subcutaneous tunnel, where one end of the graft is typically placed in an artery and the other end of the graft is typically placed in a vein so as to create an anastomosis between the two blood vessels. Access to the graft for hemodialysis is then achieved by percutaneous introduction of a needle or an access tube.

Recently, several graft designs have been proposed where the grafts are made of certain materials, such as polytetrafluoroethylene (PTFE), silicone, DACRON, polyurethane, bovine, and the like. These grafts are designed to offer immediate access to the patient's vasculature with reduced complications of hematomas between the subcutaneous tissue and the graft, kinking, thrombosis, pseudoaneurysm formation, or infection. While vascular grafts offer great promise, one issue to be resolved for the success and practical utility of vascular grafts is effective subcutaneous placement of such articles.

Subcutaneous placement of vascular grafts can be problematic since the grafts can easily be destroyed if they are stretched longitudinally as such forces change the graft's material properties. Previously proposed devices and methods for subcutaneously positioning a graft include attaching a graft directly onto a trailing end of a conventional tunneling tool which creates a subcutaneous path between two blood vessels. Such methods often result in significant longitudinal forces on the graft (as the graft is constantly being pulled behind the tunneler) which may potentially destroy the graft. Moreover, such protocols may result in twisting or kinking of the graft and a loose seal between the graft and the subcutaneous tissue as the tunnel created by the tunneler is typically of equal or larger diameter than the diameter of the vascular graft. A loose seal is undesirable as it makes it difficult to properly access the graft with a needle and increases the chances of hematomas, bleeding, and infection. Other proposed methods employ feeding a graft into a hollow tunneler or tube that is already positioned within the subcutaneous tunnel. Similarly, passing the graft into a hollow tube as well as removing the tube after the graft is positioned often results in significant longitudinal forces on the graft which compromise its structural integrity. In such instances, a loose seal is also created between the graft and the subcutaneous tissue as the diameter of the hollow tube will generally be greater than the diameter of the vascular graft to allow for release of the graft.

For these reasons, it would be desirable to provide devices, systems, and methods for positioning an article, such as a graft or catheter, in a subcutaneous tunnel between skin and muscle tissue of a patient to establish improved access to the patient's vascular system for hemodialysis, hemofiltration, or other extracorporeal blood treatments. In particular, it would be desirable if such devices, systems, and methods would minimize the friction or longitudinal forces acting against the vascular graft as it is being subcutaneously positioned. It would be further desirable if such devices, systems, and methods could provide a tighter seal between the graft and the subcutaneous tissue, minimize hematomas and infections, and enhance needle accessibility of the graft for extracorporeal treatment. The placement devices, systems, and methods should also allow for rotation of the graft without kinking or twisting complications. At least some of these objectives will be met by the devices, systems, and methods of the present invention described hereinafter.

2. Description of the Background Art

U.S. Pat. No. 4,453,928 describes a catheter tunneling apparatus where a catheter is passed into a hollow tube which is already positioned within a subcutaneous tunnel by a conventional tunneler. U.S. Pat. No. 5,300,106 describes insertion and use of a tunneling tool. Vascular grafts are described in U.S. Pat. Nos. 4,409,172; 4,604,762; 4,675,361; 4,731,073; 4,861,830; 5,840,240; and 5,886,217. The full disclosures of each of the above references are incorporated herein by reference.

BRIEF SUMMARY OF THE INVENTION

The present invention provides devices, systems, and methods for positioning an article, such as a graft or catheter, in a subcutaneous tunnel between skin and muscle tissue of a patient to establish improved access to the patient's vascular system, particularly peripheral blood vessels, for performing extracorporeal treatment on circulating blood. Exemplary extracorporeal treatment procedures include hemodialysis, hemofiltration, hemodiafiltration, plasmapheresis, apheresis, and the like. In particular, the present invention provides devices, systems, and methods which minimize longitudinal forces or friction acting against the vascular graft as it is being subcutaneously positioned while still providing a tight seal between the graft and the subcutaneous tissue, which in turn minimizes hematomas, bleeding, and infections and enhances needle accessibility of the graft for extracorporeal treatment. Moreover, the devices, systems, and methods of the present invention allow for rotation of the graft without kinking or twisting complications.

According to a first aspect of the present invention, a sheath for use with a tunneling tool comprises a pair of nested tubes and a coupling element. Each nested tube has a leading end, a trailing end, and a longitudinal opening or split. The coupling element is attached to the leading ends of the nested tubes and is removably attachable to a conventional tunneling tool. The nested tubes engage the catheter, graft, or other structure to be implanted. For example, by providing an inner tube with a diameter the same as or slightly smaller than the diameter or width of the article to be implanted, the article will be gripped by the inner tube. An outer tube may then be slid over the inner tube to apply a radially inward "clamping" force that enhances the inner tube grip. The longitudinal splits, however, allow the tubes to be easily opened to facilitate insertion of the articles being implanted. Once the article is inserted into the sheath, the article is passed into the subcutaneous tunnel with minimal distraction. Frictionless release of the article being implanted may then be effected by removing the sheath from over the article by separating the split nested tubes within the tunnel.

The nested tubes will usually have a uniform diameter along their entire length, typically being in the range from about 1 mm to 45 mm, preferably being in the range from 3 mm to 10 mm. The lengths of the nested tubes will usually be in the range from 10 mm to 200 cm, preferably being in the range from 20 mm to 24 cm. Each longitudinal opening or split subtends a circumferential arc of the tubes in the range from about 20° to about 190°, preferably in the range from 60° to about 180°. The tubes may be formed from the same or different material. For example, the outer tube may be formed from a stiffer material while the inner tube is formed from a more expansible material. Suitable tube material includes polymer materials, such as polyethylene, polypropylene, and the like. The tubes may further be counter rotatable so that the openings can be aligned to open a passage therein or the openings can be staggered apart to close a passage therein. The coupling element may comprise a male connection and a female sleeve, wherein the male connection is received within the female sleeve. In some instances the male connection may be threaded and/or knurled to provide a secure coupling between the nested tubes and the tunneling tool. The male connection and female sleeve may be formed from stainless steel, plastic, or like materials.

In another aspect of the present invention, a system for positioning an article in a subcutaneous tunnel between skin and muscle tissue of a patient comprises a tunneling tool, a pair of nested tubes coupleable to a trailing end of the tunneling tool, and a flexible article which can be slidably received within the pair of nested tubes. The nested tubes, as described above, each have a leading end, a trailing end, and a longitudinal opening. The tunneling tool may be any conventional tunneler that comprises a shaft like structure suitable for creating a subcutaneous tunnel between skin and muscle tissue of a patient. Generally, the tunnel therein lies a short distance beneath the surface of the patient's skin, typically being within 0.5 mm to 4.0 mm from the skin's surface. The article may comprise a catheter or preferably an arteriovenous graft, such as the Perma-Seal™ graft available from Possis Medical, Inc. and the VAG™ graft available from Thoratec Laboratories Corporation. One end of the graft, which may optionally have a cuff or hood on an end thereof, may be placeable in a vein and the other end of the graft may be placeable in an artery so as to create an anastomosis between the two blood vessels.

The present system advantageously minimizes longitudinal forces or friction acting against the vascular graft as it is being subcutaneously positioned. In particular, the split tubes structure inhibits graft distraction as the graft is passed and released in the subcutaneous tunnel, which in turn reduces trauma to the graft and discomfort to the patient. In some instances, at least one tube may be made from a memory alloy material or have a spring mechanism attached thereto to allow for expansion of the split tubes which in turn facilitates frictionless release of the graft. Additionally, the pair of nested tubes may be serrated along longitudinal lines to accommodate gripping of serrated articles. Moreover, the sheath structure allows the graft to be rotated within the subcutaneous tunnel without kinking or twisting complications, which is of particular benefit when utilizing hooded type grafts that need to be properly aligned with a blood vessel.

The external diameter of each nested tube will generally be equal to or slightly smaller than an expanded diameter of the flexible graft. The graft will generally have a uniform expanded diameter along its entire length, typically being in the range from about 2 mm to about 50 mm, preferably from about 4 mm to 11 mm, when the graft is made operational from vessel pressure which expands the graft. Placement of the graft in a subcutaneous tunnel that is slightly smaller than the expanded diameter of the flexible graft provides a tight and secure fit between the subcutaneous tissue and the graft. This in turn minimizes occurrences of hematomas, bleeding, and infections and enhances needle accessibility of the graft for extracorporeal treatment. The length of the graft will usually be in the range from 20 mm to 210 cm, preferably being in the range from 30 mm to 25 cm. The graft may also be trimmed to length after placement so that it is sufficiently long for the intended use. The grafts will be formed from polytetrafluoroethylene (PTFE), silicone, DACRON, polyurethane, bovine, and like materials.

In yet another aspect of the present invention, methods for subcutaneously positioning an article generally comprise providing a trailing sheath, inserting the article into the trailing sheath, and coupling the trailing sheath to a trailing end of a tunneling tool. The tunneling tool is then subcutaneously passed through the patient tissue to position the article at a desired location. The trailing sheath is then removed from over the article while the article remains at the desired location. The trailing sheath, as described above, comprises a pair of nested tubes wherein each tube has a longitudinal opening or split.

Near frictionless placement of the article at the desired location may be carried out in several fashions. For example, removing may comprise withdrawing the sheath tubes sequentially from the tunnel. Preferably, an outer tube is completely removed first from either an entrance or exit site of the tunnel followed by removal of an inner tube from the entrance or exit site. In some instances, the inner tube may be formed from a memory alloy material so that it at least partially expands after the outer tube is removed to further facilitate frictionless release of the article at the desired location. Optionally, removing may comprise withdrawing the tubes simultaneously from the tunnel in opposite directions. Still further, the tubes may be counter rotated so that the article is completely encompassed within the sheath prior to passing the tunneling tool through the patient tissue. The openings are then aligned prior to removing the sheath so that the graft remains in tact at the desired location while the sheath is removed. Any of the above protocols allow the split tubes sheath to protect the graft against longitudinal forces as the graft is subcutaneously passed and released within the tunnel. Typically, the tunneling tool will be uncoupled from the trailing sheath prior to removing the sheath. The sheath may further be rotated so that the article can be alignable with an artery or vein prior to removing the sheath. The trailing sheath may also have expansion capabilities while still encompassing the article completely prior to removing the sheath.

In still another aspect of the present invention, methods for positioning an article in a subcutaneous tunnel may comprise providing a trailing sheath having a pair of nested tubes wherein each tube has a longitudinal opening. The article is inserted into the trailing sheath and the trailing sheath is coupled to a trailing end of a tunneling tool. The tunneling tool is then subcutaneously passed through the patient tissue to position the article at a desired location. The trailing sheath is then removed from over the article while the article remains at the desired location by separating the nested tubes within the tunnel.

A further understanding of the nature and advantages of the present invention will become apparent by reference to the remaining portions of the specification and drawings.

BRIEF DESCRIPTION OF THE DRAWINGS

FIGS. 9A–9H illustrate a method according to the present invention employing the device of FIG. 1.

DETAILED DESCRIPTION OF THE INVENTION

The present invention provides devices, systems, and methods for positioning an article, such as a graft or catheter, in a subcutaneous tunnel between skin and muscle tissue of a patient to establish improved access to the patient's vascular system, particularly peripheral blood vessels, for performing hemodialysis, hemofiltration, or other extracorporeal blood treatments. In particular, the present invention provides devices, systems, and methods which minimize longitudinal forces or friction acting against the vascular graft as it is being subcutaneously positioned while still providing a tight seal between the graft and the subcutaneous tissue, which in turn minimizes hematomas, bleeding, and infections and enhances needle accessibility of the graft for extracorporeal treatment.

Figure 1:
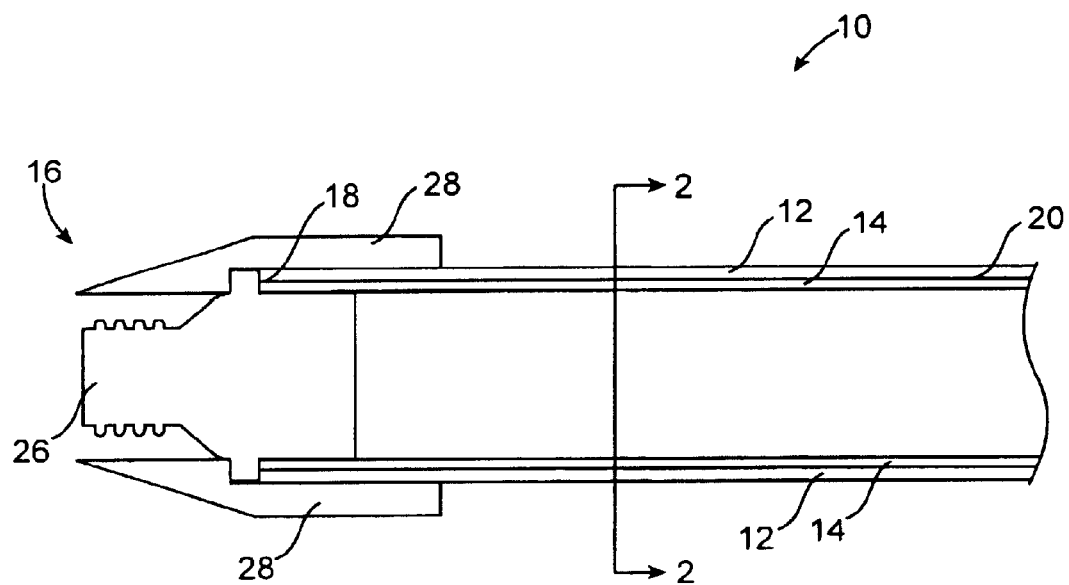
FIG. 1 is a cross-sectional view of an exemplary device for positioning an article in a subcutaneous tunnel constructed in accordance with the principles of the present invention.

Referring now to FIG. 1, an exemplary sheath 10 for use with a tunneling tool comprises a pair of nested tubes 12 and 14 and a coupling element 16. Each nested tube 12, 14 has a leading end 18, a trailing end 20, and a longitudinal opening 22 or split. The coupling element 16 is attached to the leading ends 18 of the nested tubes 12, 14 and is removably attachable to a conventional tunneling tool. It will be appreciated that the following depictions are for illustration purposes only and does not necessarily reflect the actual shape, size, or dimensions of the trailing sheath 10. This applies to all depictions hereinafter.

Figure 2:
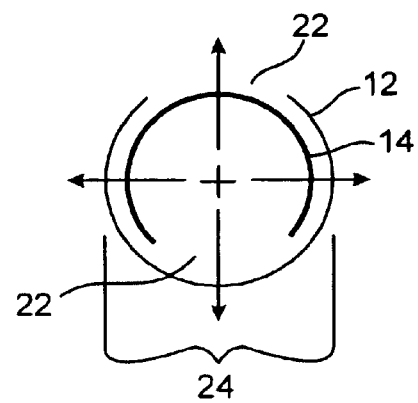
FIG. 2 is another cross-sectional view taken along line 2—2 of the sheath of FIG. 1.

Referring now to FIG. 2, the nested tubes will comprise an inner tube 14 and an outer tube 12. Each tube will usually have a uniform diameter 24 along its entire length, typically being in the range from about 1 mm to 45 mm, preferably being in the range from 3 mm to 10 mm. The lengths of the nested tubes 12, 14 will usually be in the range from 10 mm to 200 cm, preferably being in the range from 20 mm to 24 cm. Each longitudinal opening 22 or split subtends a circumferential arc of the tubes in the range from about 20° to about 190°, preferably in the range from 60° to about 180°, more preferably about 90° with the opening being separated by about 90°. The coupling element 16 may comprise a male connection 26 and a female sleeve 28, wherein the male connection 26 is received within the female sleeve 28. In some instances, the male connection 26 may be threaded and/or knurled to provide a secure coupling between the nested tubes 12, 14 and the tunneling tool. The male connection 26 and female sleeve 28 may be formed from stainless steel, plastic, or like materials.

Figure 3:
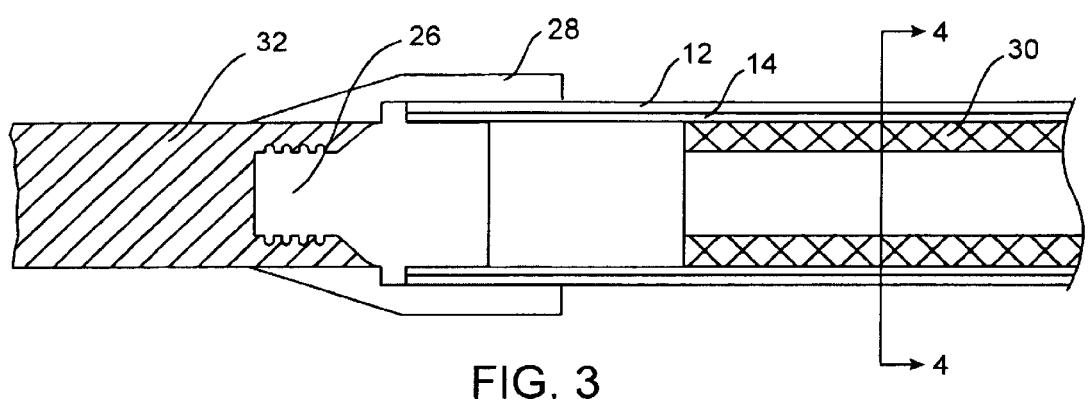
FIG. 3 is a cross-sectional view of a system for subcutaneously positioning a graft comprising a tunneling tool, a pair of nested tubes, and a flexible article.

Referring now to FIG. 3, a system for positioning an article 30 in a subcutaneous tunnel between skin and muscle tissue of a patient comprises a tunneling tool 32, a pair of nested tubes 12, 14 coupleable to a trailing end of the tunneling tool 32, and a flexible article 30 which can be slidably received within the pair of nested tubes 12, 14. The tunneling tool 32 may be any conventional tunneler that comprises a solid or hollow shaft suitable for creating a subcutaneous tunnel between skin and muscle tissue of a patient.

Figure 4:
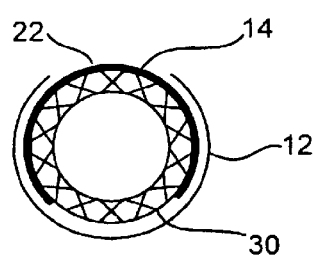
FIG. 4 is another cross-sectional view taken along line 4—4 of the sheath of FIG. 3.
Figure 5:
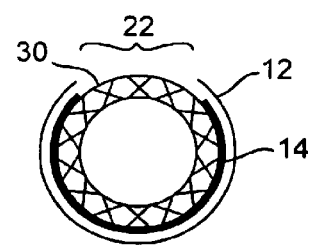
FIG. 5 is a cross-sectional view illustrating alignment of the sheath openings.
Figure 6:
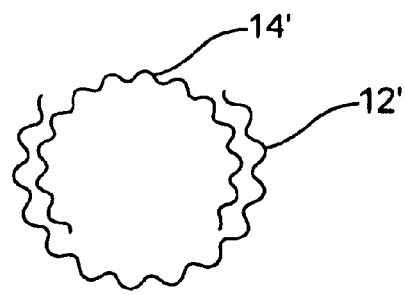
FIG. 6 is a cross-sectional view of a serrated sheath.

The nested tubes 12, 14 will have lengths, lumen diameters, and other dimensions as generally set forth above. Referring now to FIGS. 4 and 5, the tubes 12, 14 may be counter rotatable so that the openings 22 can be staggered apart, preferably by about 90°, to completely encompass the article 30 within the sheath (FIG. 4). The tubes may also be counter rotated so the that openings 22 can be aligned to open a passage for the article 30, as shown in FIG. 5. With reference to FIG. 6, the pair of nested tubes 12', 14' may also be serrated to accommodate placement of serrated articles.

Figure 7:
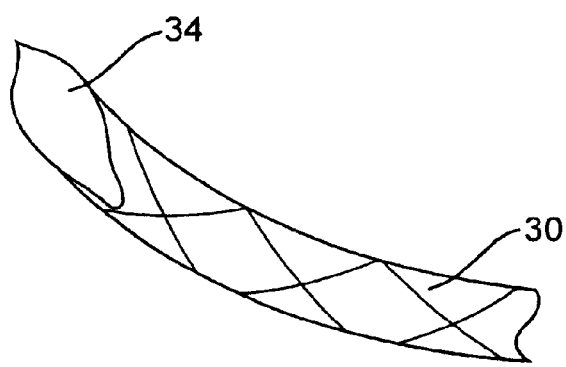
FIG. 7 is a perspective view of a hooded graft which may be used in conjunction with the present invention.
Figure 8:
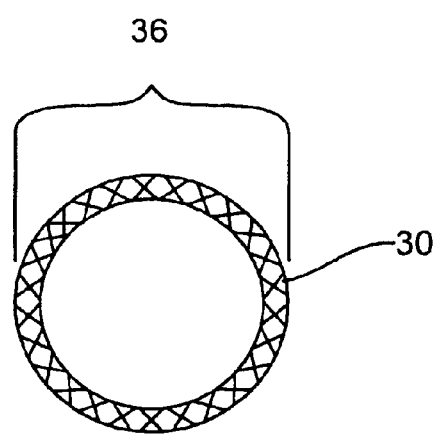
FIG. 8 is a cross-sectional view of the graft of FIG. 7.

Referring now to FIGS. 7 and 8, the article 30 may comprise a catheter or preferably an arteriovenous graft, such as the Perma-Seal™ graft available from Possis Medical, Inc. and the VAG™ graft available from Thoratec Laboratories Corporation. One end of the graft 30 may be placeable in a vein and the other end of the graft may be placeable in an artery so as to create an anastomosis between the two blood vessels. As illustrated in FIG. 7, the graft 30 may have a hood 34 or cuff on an end thereof which becomes ingrown in the vessel tissue. With reference to FIG. 8, an expanded diameter 36 of the flexible graft 30 will generally be equal to or slightly larger than the external diameter of each nested tube 12, 14. The graft 30 will have a uniform expanded diameter 36 along its entire length, typically being in the range from about 2 mm to about 50 mm, preferably from about 4 mm to 11 mm, when the graft is made operational from vessel pressure which expands the graft. Placement of the graft in a subcutaneous tunnel that is slightly smaller than the expanded diameter of the flexible graft provides a tight and secure fit between the subcutaneous tissue and the graft. This in turn minimizes occurrences of hematomas, bleeding, and infections and enhances needle accessibility of the graft for extracorporeal treatment. The length of the graft 30 will usually be in the range from 20 mm to 210 cm, preferably being in the range from 30 mm to 25 cm. The grafts will be formed from polytetrafluoroethylene (PTFE), silicone, DACRON, polyurethane, and like materials.

Figure 9A:
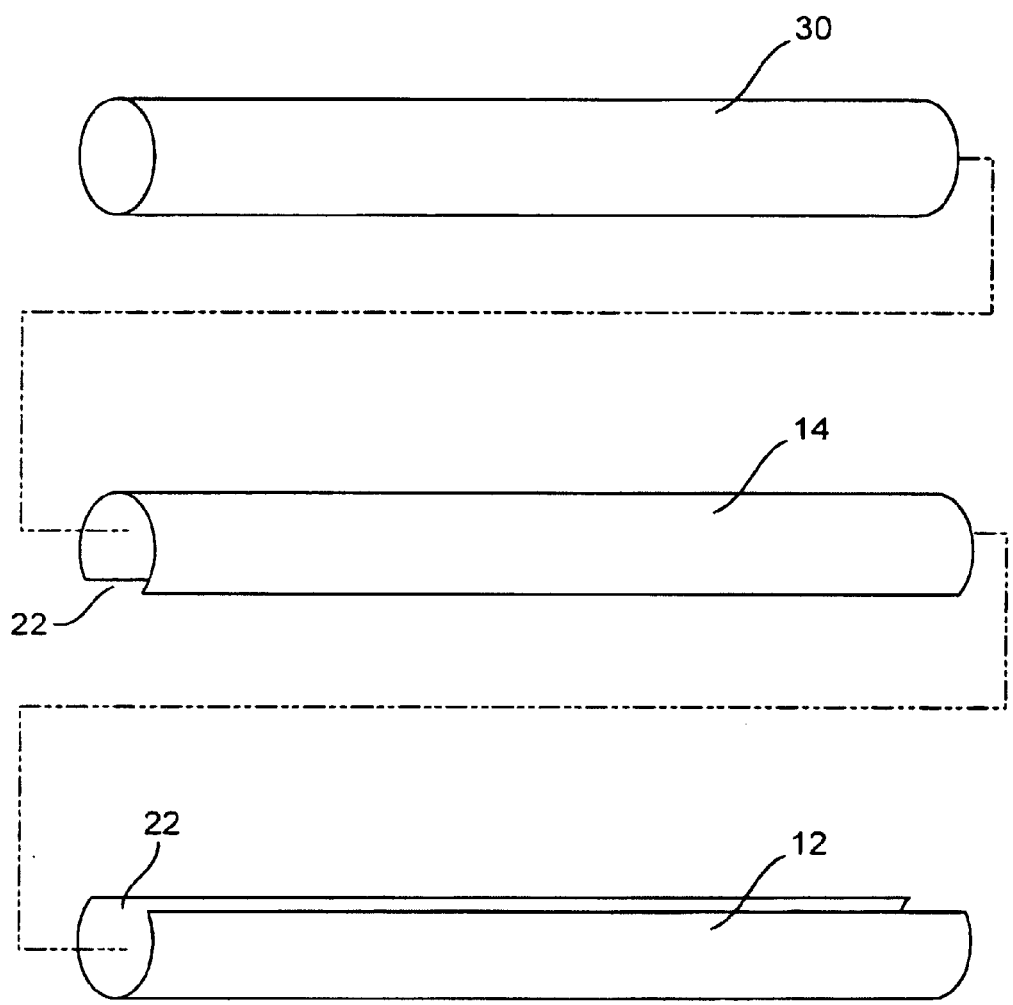
Figure 9B:
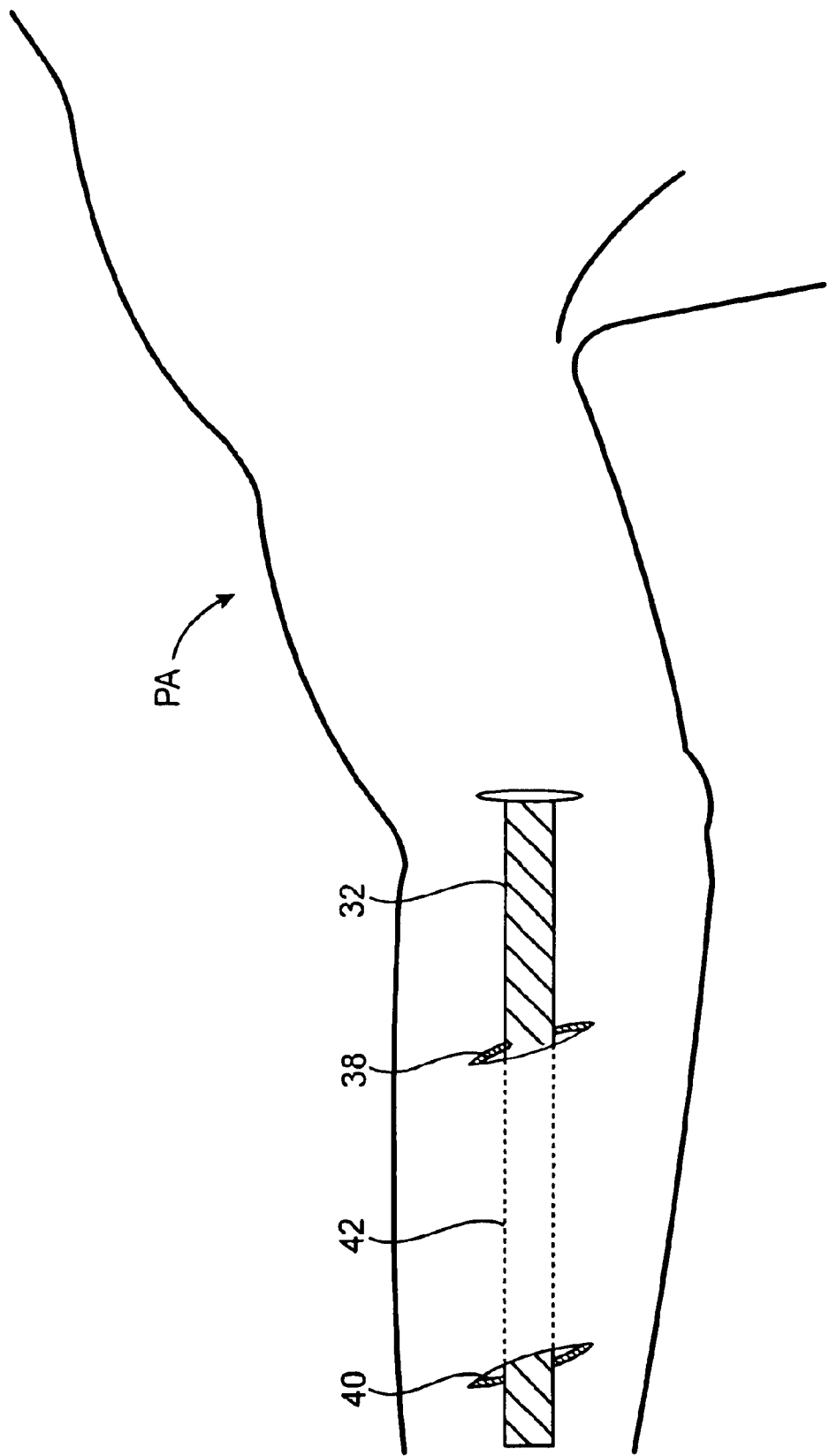
Figure 9C:
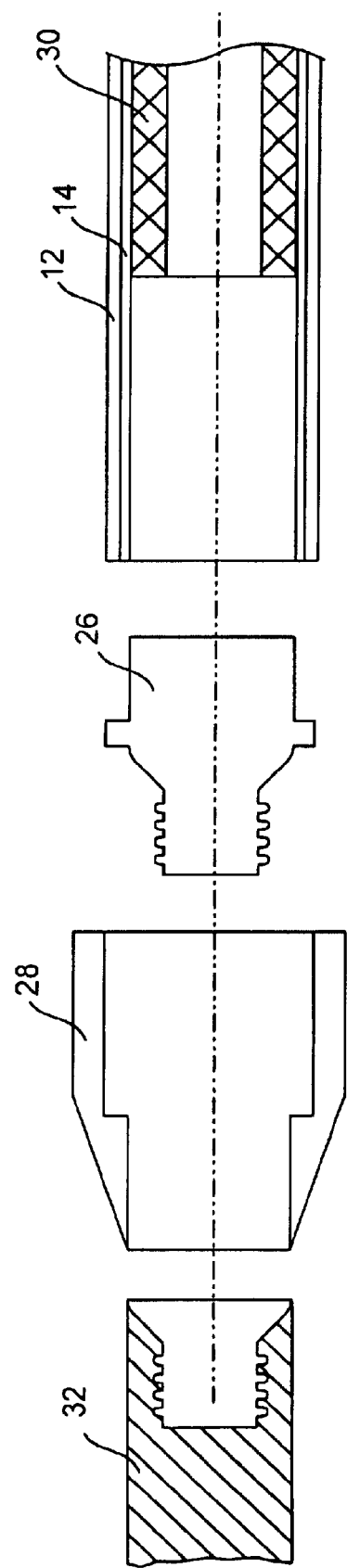
Figure 9D:
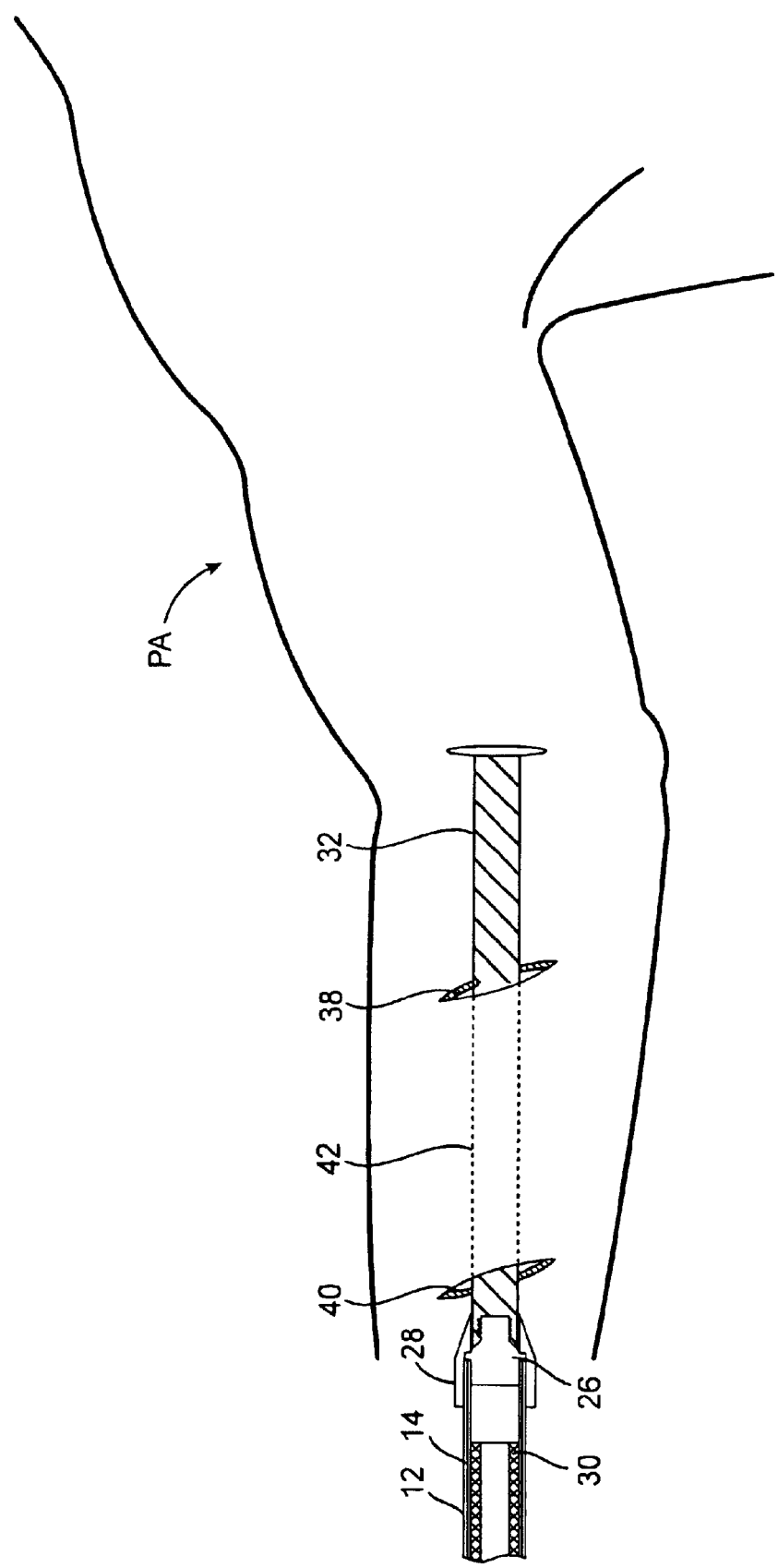

Referring now to FIGS. 9A through 9H, an exemplary method for frictionless placement of a graft in a subcutaneous tunnel with the device of FIG. 1 will be described. As illustrated in FIG. 9A, the graft 30 is inserted into a trailing sheath having a pair of nested tubes 12, 14 by first placing the graft in the clear inner tube 14 via opening 22. The inner tube 14 grips the graft 30 as the inner tube diameter is the same as or slightly smaller than the diameter of the graft to be implanted. The red outer tube 12 then slides over the clear inner tube 14 (with the tube openings being separated by about 90°) and applies a radially inward "clamping" force that enhances the inner tube grip. The longitudinal splits 22, however, allow the tubes to be easily opened to facilitate insertion of the graft. The graft 30 will generally be displaced by a distance of about 2 cm from the leading ends 18 of the tubes 12, 14. FIG. 9B illustrates a patient's arm PA in which the graft 30 will preferably be positioned to establish improved access to the patient's vascular system, particularly peripheral blood vessels in the forearm. It will be appreciated that graft placement is not limited to the forearm, and that in some instances the graft may be positioned in the patient's leg, chest, or torso. A conventional tunneling tool 32 penetrates the patient's forearm tissue at an entrance site 38 and through an exit site 40 to create a subcutaneous tunnel 42 therebetween. Generally, the tunnel 42 therein lies a short distance beneath the surface of the patient's skin, typically being within 0.5 mm to 40 mm from the skin's surface. The conventional tunneler 32 may additionally anesthetize the penetrated tissue via an irrigator or syringe attachment. As illustrated in FIGS. 9C and 9D, the nested tubes 12, 14 together with the graft 30 are coupled to the tunneling tool 32 by coupling elements 26 and 28.

Referring now to FIG. 9E, the tunneling tool 32 is then passed through the subcutaneous tunnel 42 to position the graft 30 at a desired location. The tunneling tool 32 is uncoupled from the trailing sheath 12, 14 once the graft is positioned. The nested tubes 12, 14 may further be rotated within the subcutaneous tunnel 42 without kinking or twisting complications, which is of particular benefit when utilizing hooded type grafts that need to properly aligned with a blood vessel. The trailing sheath 12, 14 may also expand while still encompassing the graft 30 completely.

Figure 9H:
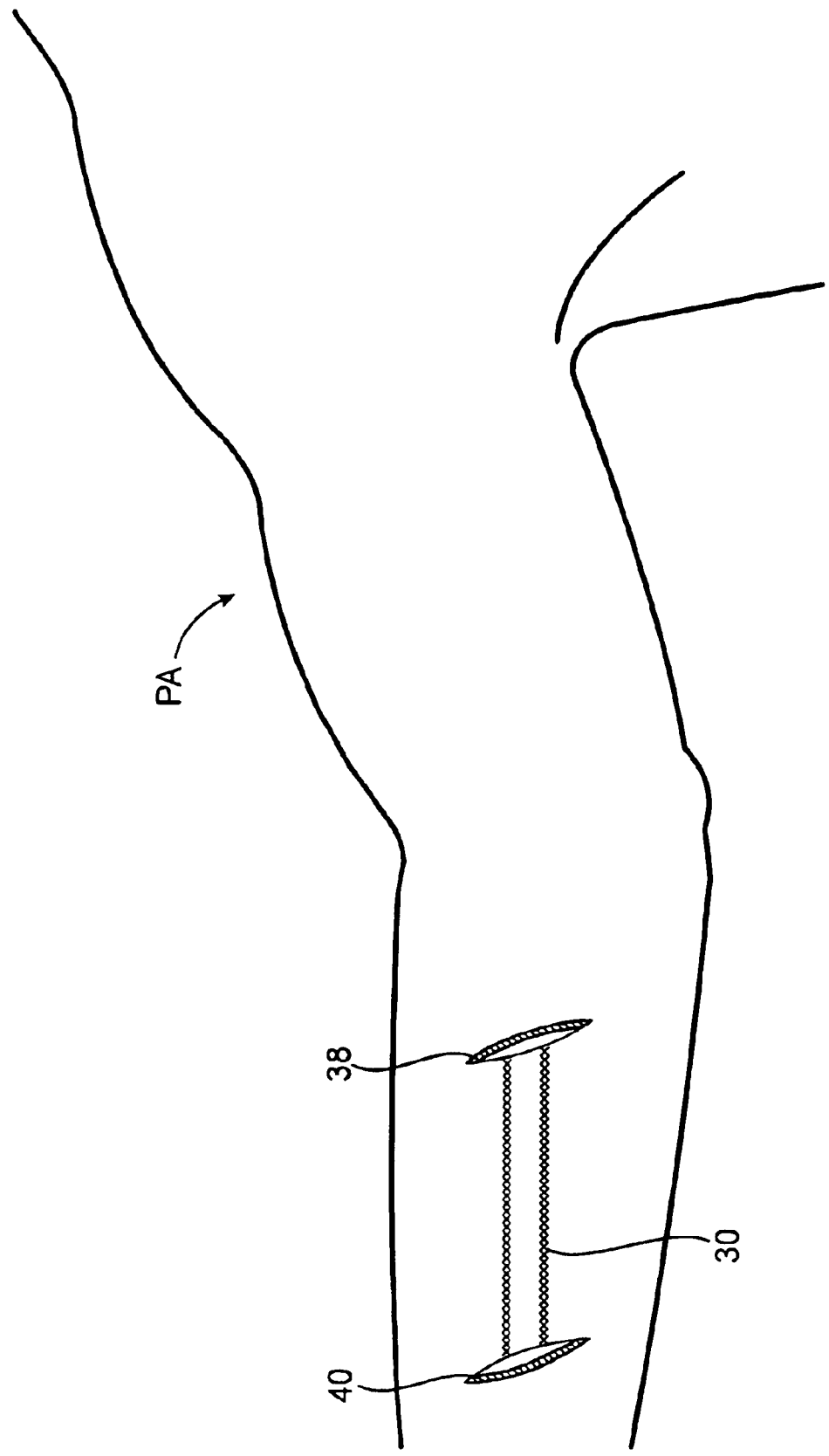

Referring now to FIGS. 9F through 9H, the trailing sheath 12, 14 is then removed from over the graft 30 while the graft remains at the desired location. Near frictionless placement of the graft at the desired location may be carried out in several fashions. Preferably, removing comprises withdrawing the nested tubes 12, 14 sequentially from the tunnel 42, wherein the outer tube 12 is completely removed first from either the entrance 38 or exit site 40 of the tunnel 42 (FIG. 9F) followed by removal of the inner tube 14 from the entrance 38 or exit site 40 (FIG. 9H). The graft 30 may then be trimmed to length after placement and extracorporeal blood flow established by accessing the graft with a needle. The present invention advantageously minimizes longitudinal forces or friction acting against the vascular graft as it is being subcutaneously positioned. In particular, the tubular sheath inhibits graft distraction as it is being passed into the tunnel and separating the split nested tubes 12, 14 within the tunnel 42 allows for near frictionless release of the graft at the desired location. With reference to FIG. 9G, the inner tube 14 may be formed from a memory alloy material or have a spring mechanism attached thereto so that the inner tube 14 at least partially expands after the outer tube 12 is removed to further facilitate frictionless release of the graft 30 at the desired location.

Alternatively, removing may comprise withdrawing the tubes 12, 14 simultaneously from the tunnel 42 in opposite directions. For instance, the outer tube 12 may be withdrawn from the entrance site 38 while the inner tube 14 is withdrawn from the exit site. Still further, the tubes may be counter rotated (to close a passage therein) so that the graft is completely encompassed within the sheath prior to passing the tunneling tool through the patient tissue to facilitate insertion of the graft (FIG. 4). The openings 22 are then aligned in the tunnel (to open a passage therein) prior to removing the sheath so that the graft remains in tact at the desired location while the sheath is removed (FIG. 5). Any of the above protocols allow the trailing sheath to protect the graft against longitudinal forces as it is subcutaneously passed and positioned within the tunnel.

Although certain preferred embodiments and methods have been disclosed herein, it will be apparent from the foregoing disclosure to those skilled in the art that variations and modification of such embodiments and methods may be made without departing from the true spirit and scope of the invention. Therefore, the above description should not be taken as limiting the scope of the invention which is defined by the appended claims.

What is claimed is:

1. A system for positioning an article in a subcutaneous tunnel between skin and muscle tissue of a patient, the system comprising:

a tunneling tool having a leading end and a trailing end;

a pair of nested tubes coupled to the tunneling tool at a location adjacent to the trailing end, each tube having a longitudinal opening;

a flexible article which can be slidably received within the pair of nested tubes.

2. A system as in claim 1, wherein the article comprises a catheter or graft.

3. A system as in claim 1, wherein the article is attachable to an artery or vein.

4. A system as in claim 1, wherein the article has a cuff or hood on an end thereof.

5. A system as in claim 1, wherein an external diameter of each tube is slightly smaller than an expanded diameter of the flexible article.

6. A system as in claim 1, wherein an external diameter of the each tube is in the range from about 1 mm to about 45 mm.

7. A system as in claim 1, wherein an expanded diameter of the article is in a range from about 2 mm to about 50 mm.

8. A system as in claim 1, wherein each longitudinal opening subtends a circumferential arc of the tubes in a range from about 20° to about 190°.

9. A system as in claim 1, wherein at least one tube is made from a memory alloy material.

* * * * *